United States Patent
Tufts

(10) Patent No.: US 11,202,863 B2
(45) Date of Patent: Dec. 21, 2021

(54) METHOD AND APPARATUS FOR INJECTING A NEUROTOXIN INTO A LOCALIZED AREA

(71) Applicant: Leslie Tufts, West Barnstable, MA (US)

(72) Inventor: Leslie Tufts, West Barnstable, MA (US)

(*) Notice: Subject to any disclaimer, the term of this patent is extended or adjusted under 35 U.S.C. 154(b) by 0 days.

(21) Appl. No.: 17/150,717

(22) Filed: Jan. 15, 2021

(65) Prior Publication Data

US 2021/0162132 A1 Jun. 3, 2021

Related U.S. Application Data

(63) Continuation of application No. 16/490,858, filed as application No. PCT/US2018/055706 on Oct. 12, 2018, now Pat. No. 11,103,642.

(60) Provisional application No. 62/571,364, filed on Oct. 12, 2017.

(51) Int. Cl.
| | |
|---|---|
| *A61M 5/31* | (2006.01) |
| *A61J 1/20* | (2006.01) |
| *A61K 38/48* | (2006.01) |
| *A61M 5/315* | (2006.01) |
| *A61M 5/32* | (2006.01) |

(52) U.S. Cl.
CPC .......... *A61M 5/3129* (2013.01); *A61J 1/2096* (2013.01); *A61K 38/4893* (2013.01); *A61M 5/31511* (2013.01); *A61M 5/329* (2013.01); *A61M 2005/3126* (2013.01)

(58) Field of Classification Search
CPC ........ A61M 2005/3126; A61M 5/3129; A61M 5/329; A61M 5/31511; A61K 38/4893; A61J 1/2096
See application file for complete search history.

(56) References Cited

U.S. PATENT DOCUMENTS

| | | | |
|---|---|---|---|
| 2009/0177156 A1* | 7/2009 | MacLean | A61M 5/3155 604/135 |
| 2009/0299328 A1* | 12/2009 | Mudd | A61M 5/31575 604/506 |
| 2014/0332555 A1* | 11/2014 | Muller | A61M 5/2425 222/41 |
| 2015/0057608 A1* | 2/2015 | Hitscherich, Jr. | A61M 5/19 604/91 |
| 2015/0060462 A1* | 3/2015 | Colbert | A61M 5/002 220/553 |
| 2016/0279345 A1* | 9/2016 | De Beer | A61M 5/002 |
| 2017/0056603 A1* | 3/2017 | Cowan | A61M 5/315 |

* cited by examiner

*Primary Examiner* — Lauren P Farrar
(74) *Attorney, Agent, or Firm* — Brown Rudnick LLP; Thomas C. Meyers

(57) ABSTRACT

A syringe assembly for administration of a neurotoxin, the syringe assembly comprising: a syringe comprising: a clear syringe barrel with dosage markings completely encircling the clear syringe barrel; and a plunger having a plunger body and a clear inverted plunger tip; and a needle assembly comprising a needle and a sealing hub for removably attaching the needle assembly to the syringe, wherein the needle is approximately 0.15 inches to approximately 0.3 inches in length and has a gauge of approximately 27 gauge to approximately 35 gauge.

15 Claims, 6 Drawing Sheets

METHOD AND APPARATUS FOR INJECTING A NEUROTOXIN INTO A LOCALIZED AREA

CROSS-REFERENCE TO RELATED APPLICATIONS

The present application is a continuation of U.S. application Ser. No. 16/490,858, filed Sep. 3, 2019, which is a 371 national stage entry of international PCT Application No. PCT/US2018/055706, filed Oct. 12, 2018, which claims priority to U.S. Provisional Patent Application No. 62/571,364, filed Oct. 12, 2017, the contents of each of which are incorporated by reference herein in their entireties.

FIELD OF THE INVENTION

This invention relates to syringe assemblies in general, and more particularly to methods and apparatus for injecting a neurotoxin into a localized area.

BACKGROUND OF THE INVENTION

Botulinum toxin is a neurotoxic protein produced by a number of different bacterial species, including *Clostridium botulinum*. Although it is a powerful neurotoxin, botulinum has been developed for a number of therapeutic and cosmetic uses, the most prominent being Botox® injections for cosmetic alteration of skin. Botox® reduces facial wrinkles and other fine lines in the skin by paralyzing muscles and is commonly used for injection in the forehead and around the eyes. Botox® is also used to treat eye squints, excessive sweating, migraines and some bladder and bowel disorders.

The botulinum toxin is typically stored in a powdered form in a glass container with a rubber seal until it is time to administer the botulinum toxin to a patient. At that time, saline is added to the botulinum toxin powder to form a solution (i.e, to reconstitute the botulinum toxin), and the solution is drawn into a syringe barrel for intramuscular injection through a needle.

While some clinicians manually remove the rubber seal with a bottle opener-type device to reconstitute the botulinum toxin, and then use a syringe to draw the botulinum toxin into the syringe barrel, this is not a preferred method of loading a syringe since (i) it is more difficult to draw the botulinum toxin into the syringe barrel when the container cannot be flipped over because the top of the container is open, and (ii) the process of opening the sealed container can contaminate the botulinum toxin.

Accordingly, it is preferred to keep the rubber seal on the container, and then use a needle to pierce through the rubber seal and draw up the botulinum toxin into the syringe barrel. In order to draw the botulinum toxin solution into the syringe barrel, the needle must be long enough and thick enough to pierce through the rubber seal of the glass container holding the botulinum toxin solution without bending the needle. Conventional loading and delivery of botulinum toxin is generally accomplished with a syringe having a 27 to 32 gauge needle that is typically 0.5 inches in length (but may be longer). This permits the needle to load the botulinum toxin into the syringe without bending the needle, however, the long length of the needle can penetrate too deep into the unintended musculature of the patient.

A significant problem in the administration of botulinum toxin in cosmetic procedures occurs when the needle penetrates too deeply into the musculature. This is significant because the botulinum toxin spreads in a 1 cm radius around the injection site once it has been injected into the patient. It is highly important that the needle be injected at the exact depth for treatment (i.e., at 0.25 inches) so as to prevent the botulinium toxin from acting on an unintended muscle. For example, pstosis (droopy eyelids) is a common side effect and is due primarily to migration of the botulinium toxin from its intended site to the levator palpebrae superioris muscle. The levitator palpebrae muscle allows the eyelid to open fully, and the botulinum toxin can paralyze this muscle, resulting in ptosis.

Another common treatment area for neurotoxins is the forehead. Ptosis of the brow can inadvertently occur here as well when a long needle is used to deliver the botulinium toxin to the forehead. If the zygomaticus major and minor are injected improperly, paralysis of the side of the face can occur, and the patient appears as though he or she has suffered a stroke. Injecting too deeply into the orbicularis ori muscle may interfere with its function as well. Where injection is too deep into the orbicularis ori muscle, the patient will experience difficulty talking, drinking and/or eating.

For the treatment of Crows Feet, injections are typically administered subdermally, however, when a long and large gauge needle is used, the needle may penetrate beyond the desired subdermal injection site, which may result in diffusion of the neurotoxin outside of the desired injection site.

Clinicians attempt to limit excessive penetration of the needle and migration of the neurotoxin by careful technique, which may include manually controlling the depth of needle insertion, typically with the clinician's non-dominant hand (i.e., the hand not holding the syringe). However, with a typical 0.5 inch needle, there remains a significant risk of ptosis and other unwanted side effects due to excessive penetration of the needle into the site of injection.

Given the significant risk of ptosis and other side effects from excessive needle penetration, a need exists for a syringe assembly having a needle which is long enough and strong enough to pierce through the rubber seal covering the glass container storing the botulinium toxin in order to draw up the botulinium toxin into the syringe barrel, but short enough and fine enough that the needle does not penetrate too deep into the musculature of the patient during injection of the botulinium toxin.

Furthermore, each time a needle passes through an object (e.g., the rubber seal covering the glass container storing the botulinium toxin, the skin of the patient, etc.), the needle is dulled. Since a dull needle causes more pain to a patient than a sharp needle, the needle should be replaced once it becomes dull. However, a needle on a conventional syringe for neurotoxin injections cannot be removed from the syringe. Therefore, the entire syringe assembly (i.e., the syringe and the needle) needs to be discarded when a needle is dull and needs to be replaced. Thus, there is also a need for a needle which can be removed from a neurotoxin delivery syringe so that the entire syringe assembly does not need to be replaced when the needle needs to be replaced.

In addition to the foregoing, conventional syringes used for Botox® and other neurotoxin injections have several features which can lead to inaccurate dosing of the neurotoxin.

More particularly, conventional syringes include a syringe barrel and a plunger disposed within the syringe barrel. The syringe barrel comprises a hollow, elongated body having dosage markings on the exterior of the syringe barrel. The plunger comprises a plunger body ending in a plunger tip. Both the syringe barrel and the plunger of a conventional syringe have several shortcomings.

For one thing, with a conventional syringe, the plunger tip is flat, which can trap small amounts of the neurotoxin within the needle hub, which in turn prevents the appropriate dose of neurotoxin from being completely injected into the patient and also wastes the neurotoxin product.

Furthermore, the plunger body and plunger tip have the same color, which makes it difficult to determine when the plunger tip is positioned at the appropriate dosage marking on the syringe barrel. Additionally, the color of the colored plunger tip is often distracting to a clinician and/or obstructs the clinician's view. This, in turn, may decrease the dosing accuracy.

Additionally, the dosage markings on the exterior of a conventional syringe barrel do not completely encircle the syringe barrel, thus making injecting the correct dosage of neurotoxin difficult as the dosage markings appear on only one side of the syringe barrel. More particularly, when the needle is penetrating the skin of the patient, and the dosage markings are positioned on the side of the syringe barrel facing away from the clinician, the clinician must rotate the syringe assembly until the clinician can read the dosage markings on the syringe barrel. Not only can this lead to inaccurate dosing of the neurotoxin, which can lead to ineffective treatment from the insufficient injection of neurotoxin and/or deleterious side effects from the injection of too much neurotoxin, but the twisting of the syringe assembly while the needle is positioned intramuscularly can also cause pain and discomfort to the patient as the clinician rotates the needle during injection of the neurotoxin.

The difficulty in determining how much neurotoxin is contained within the syringe barrel is enhanced because cosmetic neurotoxin injections are often given in very small amounts in multiple locations, thus requiring visualization of dosage markings during injection of the neurotoxin and not just upon syringe loading.

Furthermore, a conventional syringe often has a small storage capacity (i.e., 0.5 cc). A small storage capacity requires use of more than one syringe when injecting a neurotoxin into multiple sites on a patient, which leads to large amounts of waste and an increase in cost.

Thus, there is also a need for a new and improved syringe barrel and plunger for the local application of botulinum toxin and other neurotoxins.

In addition to the foregoing, there is currently no standard that governs the administration of neurotoxins to a patient, either with respect to the syringe assembly used by clinicians or with respect to the injection process. By way of example, some neurotoxin delivery clinicians will use syringe assemblies that are typically used for insulin delivery because those syringe assemblies have certain attributes that are useful in neurotoxin delivery, while other clinicians use syringe assemblies that are used for other types of injections. Thus, there is also a need for a universal syringe assembly that combines the preferences of each clinician into a single syringe assembly that can be consistently used by all clinicians for the delivery of neurotoxins to a patient.

SUMMARY OF THE INVENTION

The present invention provides a new and improved syringe assembly for injection of botulinum toxin and other neurotoxins or medicaments (sometimes also referred to herein as pharmaceutical compositions) into a localized area in which over-penetration of the injection and/or migration of the composition may have deleterious effects.

The syringe assembly of the present invention solves the problems associated with conventional syringe assemblies by:

(i) providing a syringe with a short removable needle, which limits the depth that a needle penetrates during injection of the neurotoxin, and which can be easily removed from the syringe;

(ii) providing a syringe with a narrow gauge needle so as to increase accuracy of the placement of the injection, reduce trauma to the patient, and reduce diffusion of the neurotoxin away from the injection site;

(iii) providing a plunger with an inverted plunger tip which reduces the amount of neurotoxin that remains in the syringe barrel after the plunger has passed through the syringe barrel to expel the neurotoxin;

(iv) providing a plunger having a plunger body with a clear plunger tip so as to provide a plunger tip which is visually distinct from the plunger body, whereby to enable a clinician to more accurately deliver the appropriate dosage of neurotoxin to a patient, without distracting the clinician with a colored plunger tip;

(v) providing a syringe barrel with dosage markings that completely encircle the syringe barrel so that the dosage markings are no longer obstructed from the clinician's view at certain angles; and (vi) providing a syringe with a larger capacity than conventional syringes.

In one preferred form of the present invention, there is provided a syringe assembly for administration of a neurotoxin, the syringe assembly comprising:

a syringe comprising:
a clear syringe barrel with dosage markings completely encircling the clear syringe barrel; and
a plunger having a plunger body and a clear inverted plunger tip; and
a needle assembly comprising a needle and a sealing hub for removably attaching the needle assembly to the syringe, wherein the needle is approximately 0.15 inches to approximately 0.3 inches in length and has a gauge of approximately 27 gauge to approximately 35 gauge.

In another preferred form of the present invention, there is provided a method for injecting a neurotoxin into a body of a patient, the method comprising:

providing a syringe assembly comprising:
a syringe comprising:
a clear syringe barrel with dosage markings completely encircling the clear syringe barrel; and
a plunger having a plunger body and a clear inverted plunger tip; and
a needle assembly comprising a needle and a sealing hub for removably attaching the needle assembly to the syringe;
attaching a first needle assembly to the syringe assembly;
passing the needle into a container of neurotoxin and drawing the neurotoxin into the syringe assembly;
removing the first needle assembly from the syringe assembly;
attaching a second needle assembly to the syringe assembly, wherein the needle of the second needle assembly is shorter and narrower than the needle of the first needle assembly; and
delivering the neurotoxin into the body of a patient.

In yet another preferred form of the present invention, there is provided a method for injecting a neurotoxin into a body of a patient, the method comprising:

providing a syringe assembly comprising:
a syringe comprising:

a clear syringe barrel with dosage markings completely encircling the clear syringe barrel; and
a plunger having a plunger body and a clear inverted plunger tip; and
a needle assembly comprising a needle and a sealing hub for removably attaching the needle assembly to the syringe;
attaching a first needle assembly to the syringe assembly, wherein the needle is approximately 0.5 inches to approximately 1.0 inches in length and has a gauge of approximately 20 gauge to approximately 27 gauge;
passing the needle into a container of neurotoxin and drawing the neurotoxin into the syringe assembly;
removing the first needle assembly from the syringe assembly;
attaching a second needle assembly to the syringe assembly, wherein the needle is approximately 0.15 inches to approximately 0.3 inches in length and has a gauge of approximately 27 gauge to approximately 35 gauge; and
delivering the neurotoxin into the body of a patient.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

The present invention provides new and improved syringe assemblies for injection of botulinum toxin and other neurotoxins or medicaments (sometimes also referred to herein as pharmaceutical compositions) into a localized area in which over-penetration of the injection and/or migration of the pharmaceutical composition may have deleterious effects.

Figure 1:
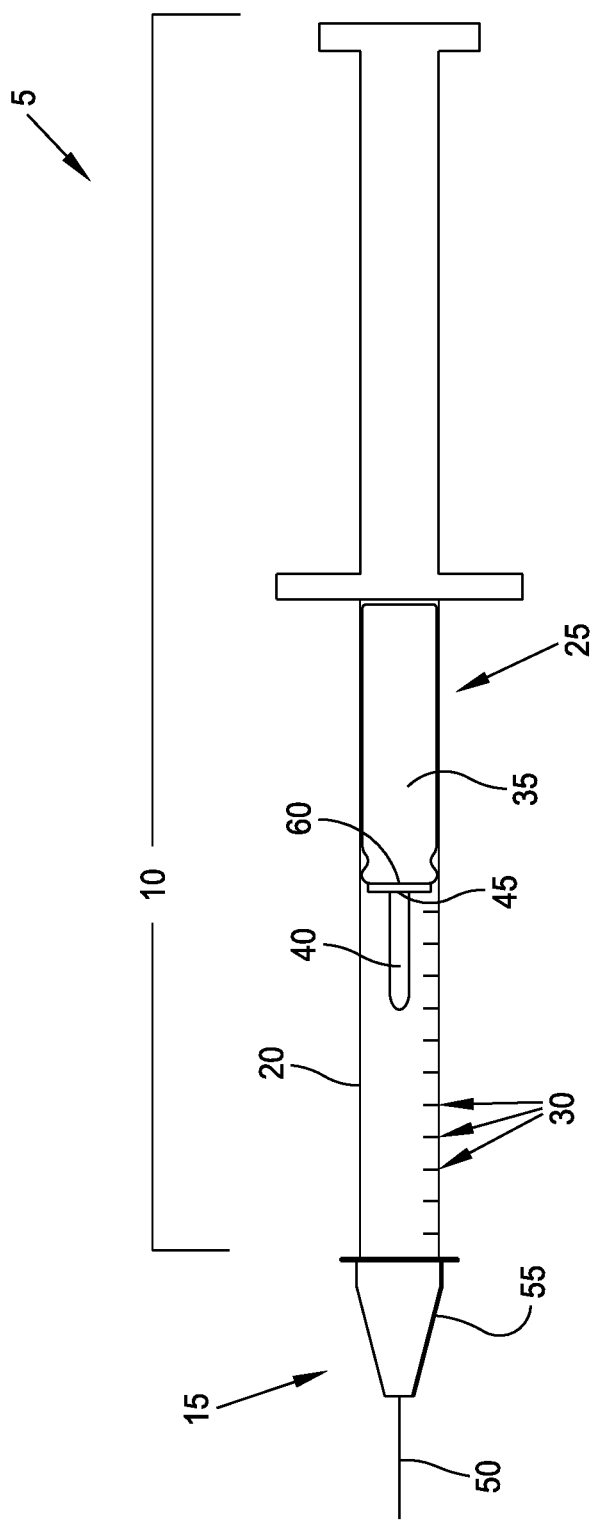
FIG. 1 is a schematic view showing a syringe assembly according to the present invention.

FIG. 1 shows an exemplary syringe assembly 5 according to the present invention. More particularly, syringe assembly 5 comprises a syringe 10 and a needle assembly 15. The needle assembly is removably attached to the distal end of syringe 10 and comprises a needle for use in the injection of neurotoxins (e.g., Botox®, Dysport® and Xeomin®) to a patient, as will be discussed in further detail below.

Syringe 10 generally comprises a syringe barrel 20 and a plunger 25 disposed within the syringe barrel. Syringe barrel 20 comprises a clear, hollow, elongated body having dosage markings 30 disposed on the exterior of the syringe barrel. Dosage markings 30 indicate the amount of neurotoxin contained within syringe barrel 20.

Plunger 25 comprises a plunger body 35 having an inverted plunger tip 40. Inverted plunger tip 40 is narrower than plunger body 35 and is specifically shaped to fit within needle assembly 15 so as to ensure that the neurotoxin is completely evacuated from syringe 10 and not trapped in needle assembly 15 (which can happen with a flat or square plunger tip).

In a preferred form of the invention, plunger body 35 is clear or opaque and plunger tip 40 is clear.

A thick dark marking 60 appears at the distal end of plunger body 35 in the area where plunger body 35 meets plunger tip 40 (i.e., junction 45) so that the end of plunger body 35 can be easily seen by a clinician as the plunger moves past the dosage markings on the syringe barrel. Marking 60 may be formed integral with plunger body 35 or plunger tip 40, or marking 60 may be a circular band or ring surrounding plunger body 35 at junction 45. Marking 60 is preferably a dark color (e.g., black) so as to be visually distinct from clear or opaque plunger body 35 and clear plunger tip 40. When marking 60 is aligned with a dosage marking 30 on syringe barrel 20, a clinician can determine the amount of neurotoxin contained within syringe barrel 20 and/or determine the amount of neurotoxin that has been delivered to the patient. Since marking 60 is visually distinct on plunger 25, it is easier for a clinician to visually control the amount of neurotoxin in syringe barrel 20, which significantly improves dosage accuracy.

Furthermore, the clear plunger tip also increases dosing accuracy as it is not distracting or obstructive to a clinician's view when performing an injection.

Needle assembly 15 comprises a needle 50 and a sealing hub 55 for attaching needle 50 to the distal end of syringe 10.

Needle 50 may be about 0.15 inches to about 0.30 inches in length and about 27 gauge to about 35 gauge in diameter. In one preferred form of the invention, needle 50 is approximately 0.25 inches in length and approximately 33 gauge in diameter. Preferably, needle 50 is beveled for ease of penetration into the intramuscular injection site of the patient.

The 0.25 inch needle allows for precise placement of the needle in the intended injection site and minimizes deep penetration and consequent diffusion of neurotoxin away from the intended site of injection. In other words, needle 50 is long enough to provide sufficient penetration into an intended intramuscular site for localized delivery of a neurotoxin, but not so long as to risk over-penetration of the needle into an unintended intrasmuscular site. Thus, needle 50 is useful for the administration of neurotoxins into the body of the patient in which localized injection and limited diffusion is important in order to minimize adverse side effects.

Sealing hub 55 is preferably formed integral with needle 50 and may be attached to the distal end of syringe 10 via a friction fit or by a screw mechanism, or in other ways well known to those skilled in the art (e.g., via a Luer Lock mechanism). Sealing hub 55 permits a needle to be removed from, and/or attached to, syringe 10. This is significant because it permits a longer, wider gauge needle (e.g., 0.5 inches or longer and 20 gauge in diameter) to be attached to syringe 10 and used to draw neurotoxin from a storage source into the syringe barrel (or to reconstitute the neurotoxin) and then the longer, wider needle can be removed from the syringe so that the shorter, narrower needle of the present invention may be used to inject the neurotoxin into the patient.

Figure 2:
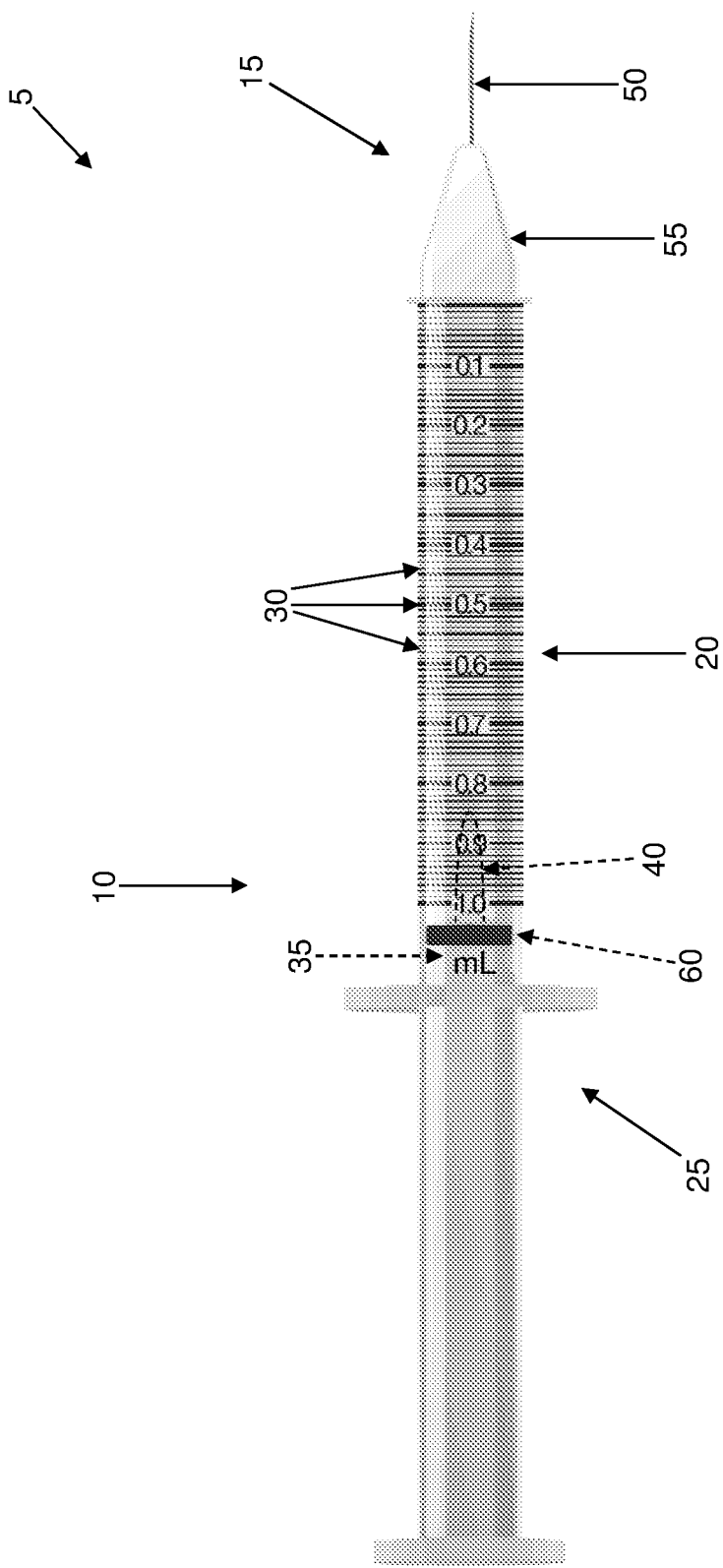
FIGS. 2-4 are schematic views showing the syringe assembly of the present invention with dosage markings extending around the entire circumference of the syringe barrel.
Figure 3:
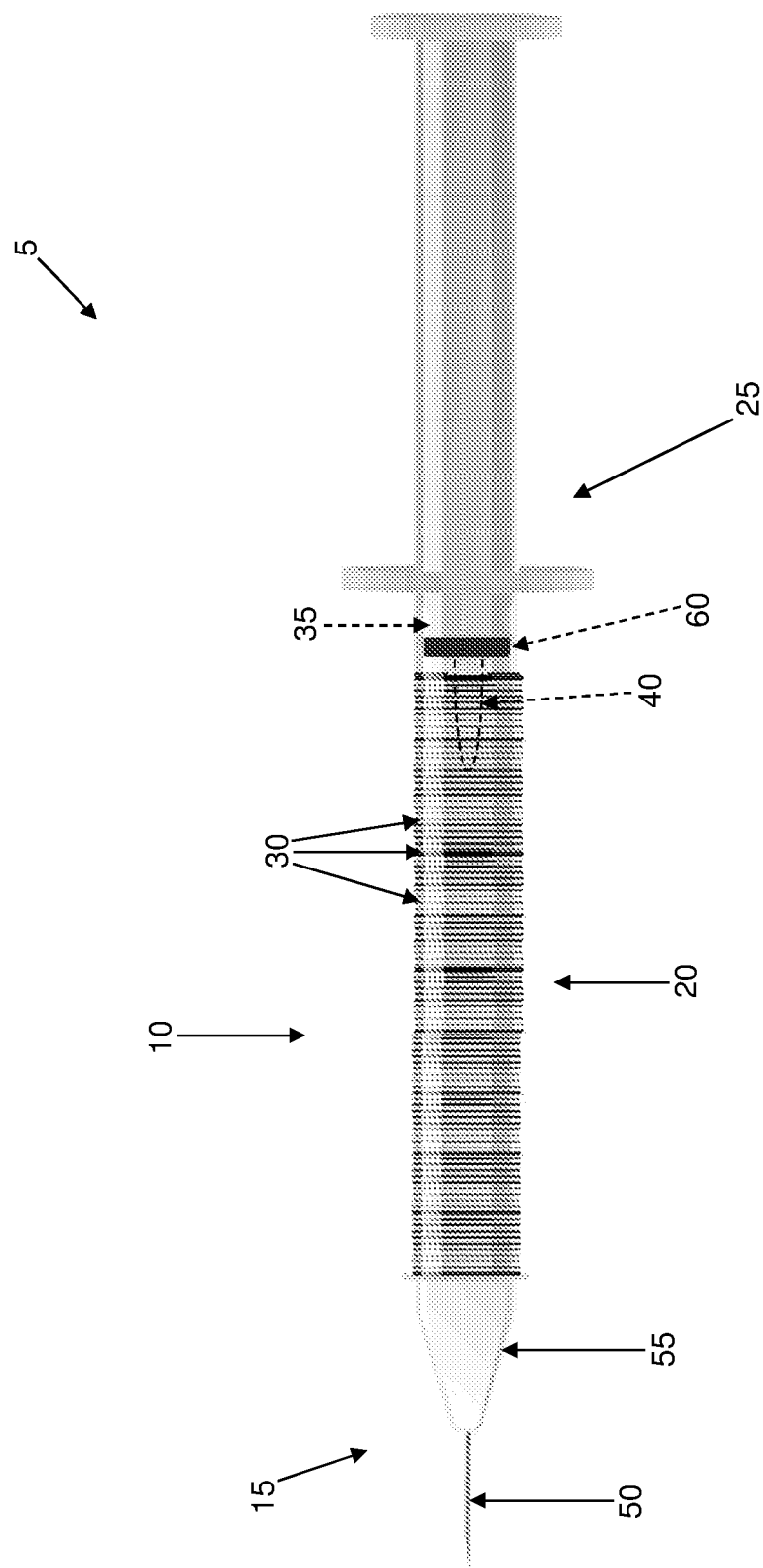
Figure 4:
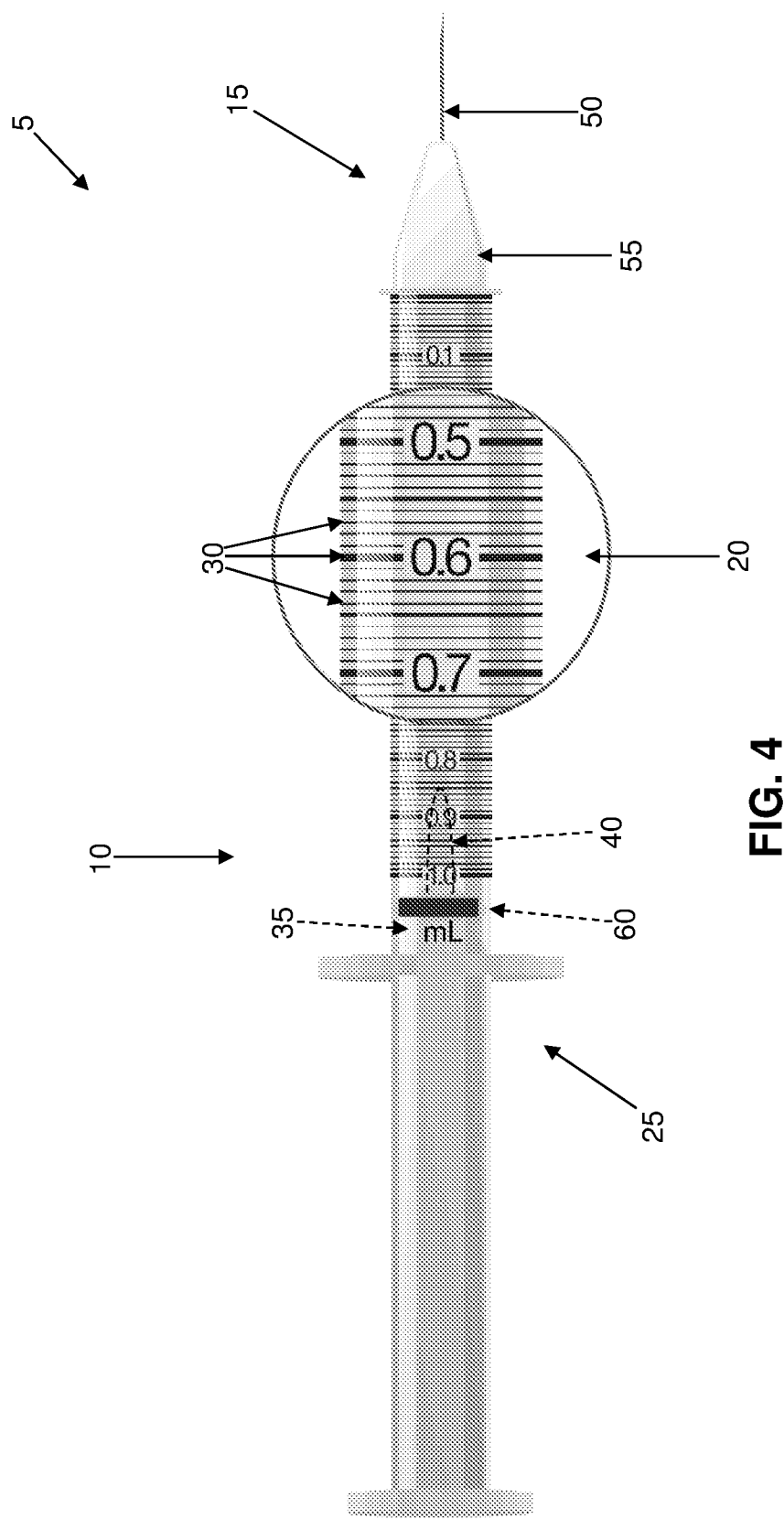
Figure 5:
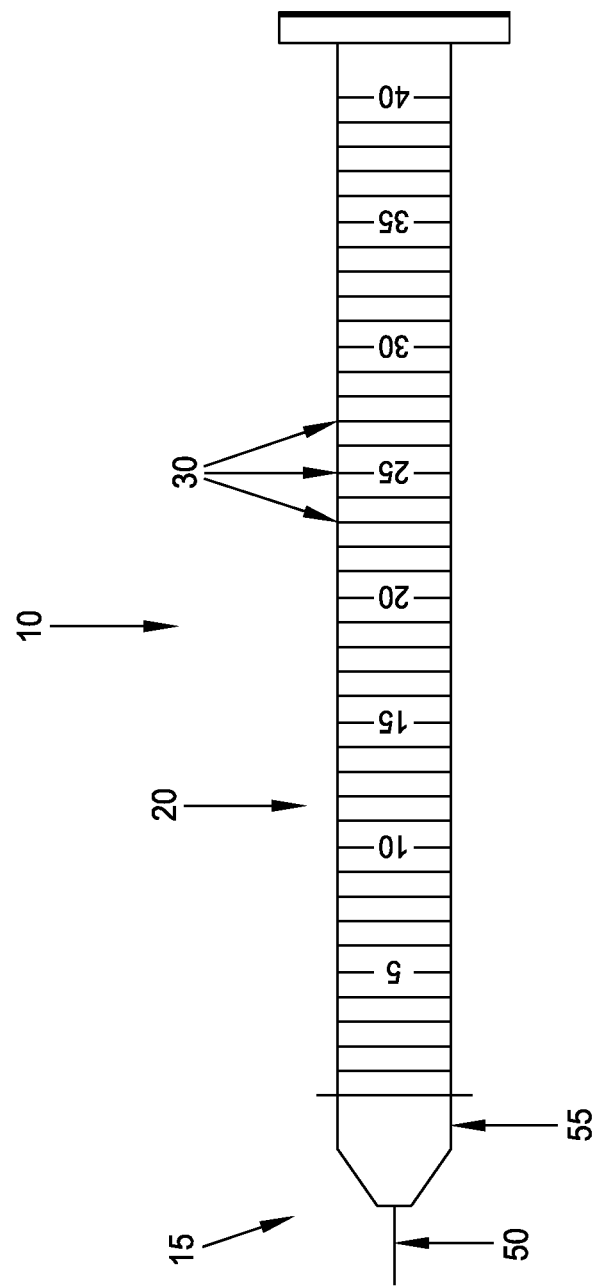
FIG. 5 is a schematic view showing the syringe assembly of the present invention with an alternative presentation of dosage markings.

Looking next at FIGS. 2-4, an alternative syringe barrel is shown. In this form of the present invention, dosage markings 30 extend around the entire circumference (i.e., 360 degrees) of clear syringe barrel 20 so as to completely encircle the syringe barrel.

In a preferred embodiment, syringe barrel 20 can hold 1.0 cc of neurotoxin, with syringe barrel 20 being clearly marked in 0.1 cc increments from the distal end of the syringe barrel to the proximal end of the syringe barrel (i.e., the area of the syringe that is proximal to where the plunger is depressed). Typically, the barrel is marked by 0.1 cc increments beginning with 0.0 cc at the distal end of the syringe barrel and ending at 1.0 cc at the proximal end of the syringe barrel.

The dosage markings are marked in a color (e.g., black) that stands out on the clear syringe barrel. In addition to the 0.1 cc increment markings, there are ten 0.01 cc markings between each 0.1 cc marking, with each line marked in black between 0 and 0.1 cc representing 0.01 cc. Preferably, the 0.05 cc level is marked in bold and/or with a larger demarcation. This bolder demarcation of the 0.05 cc level marking between each 0.1 cc measurement continues until 1.0 cc is reached.

As shown in FIG. 4, dosage markings 30 are darkest black at 0.1 cc increments, slightly lighter black at 0.05 cc increments, and lightest black at 0.01 cc increments.

Alternatively, dosage markings 30 can be orange instead of black. In this embodiment, the darkest orange is at 0.1 cc increments, slightly lighter orange at 0.05 cc increments and lightest orange at 0.01 increments. Whether black or orange (or any other color) dosage markings 30 are used on clear syringe barrel 20, plunger tip 40 should be clear and marking 60 at junction 45 should be dark black (or any other dark color) to contrast against the dosage markings and/or syringe barrel 20.

In this way, the syringe assembly of the present invention provides a syringe barrel with highly visible and unobstructed calibrations that encircle the entire circumference of the syringe barrel. This enables the clinician to clearly see the dosage markings regardless of how the syringe is held.

By way of example but not limitation, when neurotoxins are injected into a patient to treat Crows Feet, a needle having a beveled tip is typically used, and it is preferable to have the bevel side of the needle tip facing up during the injection. Having to position a needle at a certain angle is complicated when the dosage markings are only on one side of the syringe barrel because a clinician would be unable to see the dosage marking if the markings were on the opposite side of the syringe barrel. However, by providing a syringe assembly with the dosage markings encircling the entire syringe barrel, a clinician does not have to worry whether or not the dosage markings will be visible when the bevel of the needle tip is facing up, since the dosage markings will always be visible at any angle.

Thus, the provision of a syringe barrel having dosage markings that completely encircle the syringe barrel is a significant improvement over conventional syringe assemblies because the dosage markings are now visible to the clinician along the entire circumference of the syringe barrel, regardless of how the syringe is held. This significantly improves the dosing accuracy since a clinician no longer has to turn the syringe in order to read the dosage markings on one side of the syringe in order to determine the amount of neurotoxin contained within the syringe barrel. This also leads to less discomfort for the patient as turning the needle once it has been injected causes unnecessary trauma to the patient.

Looking now at FIG. 5, an alternative presentation of dosage markings is provided on syringe barrel 20. In this embodiment, the syringe barrel is similar to the syringe barrel of FIGS. 1-4, but the cc (or mL) line increments have been replaced with units ranging from 1 unit to 40 units. More particularly, the first line at the distal end of the syringe barrel refers to 1 unit, and the proximal end of the syringe barrel is labeled 40 units, with each line marking increasing by 1 unit between 1 unit and 40 units, and with each line marking extending around the entire circumference of the syringe barrel. While the units are shown in black, it is important to note that any color which is visible on the syringe barrel may be used (e.g., orange). It is also important to note that there is no need to vary the shading of the colors since each line marking equals 1 unit.

Marking the syringe barrel with units instead of cc's or mL's is significant because Botox® dosing is typically provided in units, with each 5 units of Botox® equaling 0.1 cc. When the dosage markings on the syringe barrel are presented as cc's or mL's, a clinician first has to calculate the number of cc's that correspond to the number of units to be injected for each dose of Botox® (e.g., if 10 units are to be injected, the clinician must convert the 10 units into cc's before delivery to the patient, rather than simply delivering 10 units of Botox® to the patient). By replacing the cc markings with units, a clinician can skip the extra step of calculating the number of cc's per unit of Botox®—a clinician simply injects the number of units suggested for the Botox® injection.

The syringe assembly of the present invention is generally used as follows:

(i) the syringe assembly is fitted with a longer/wider gauge needle, and the longer/wider gauge needle is used to draw neurotoxin from a storage container and into the syringe;

(ii) the longer/wider gauge needle is removed from the syringe assembly and replaced with a shorter/narrower gauge needle;

(iii) the syringe assembly with the shorter/narrower gauge needle is used to administer neurotoxin to a patient;

(iv) the shorter/narrower gauge needle is replaced as needed during administration of the neurotoxin into multiple injection sites; and (v) the syringe assembly is discarded once the procedure is completed.

More particularly, when a neurotoxin is to be administered into a localized area of a patient, syringe assembly 5 may be used. First, an appropriate size syringe 10 (e.g., 1.0 cc) is chosen and sealing hub 55 is used to secure an appropriately sized first needle 50 to the distal end of syringe 10. First needle 50 may be long and wide (e.g., 0.5 inches and 20 gauge) so as to draw neurotoxin from a storage container and into syringe 10 quickly and/or to allow for reconstitution of the neurotoxin in syringe 10 (e.g., diluting 100 units of the neurotoxin, Botox®, with 2.5 cc of bacteriostatic saline). Once the desired amount of neurotoxin is drawn into syringe 10, first needle 50 is removed from syringe 10. It should be appreciated that dosage markings 30 (in combination with marking 60 at junction 45) are used to visually indicate to the user when the desired amount of neurotoxin is in syringe 10.

Next, a second needle 50 which has a shorter length and narrower gauge (e.g., 0.25 inches and 33 gauge) than first needle 50 is connected to syringe 10 via sealing hub 55. It should be appreciated that second needle 50 is long enough to provide sufficient penetration into an intramuscular site for localized delivery of the neurotoxin, but not so long as to risk over-penetration of the needle into an unintended intramuscular site, and second needle 50 is narrower than a conventional neurotoxin injection needle so as to allow for more precise placement of the injection, decreased diffusion of the neurotoxin and decreased pain to the patient. Once second needle 50 has been connected to syringe 10, syringe assembly 5 is ready for use on a patient.

Second needle 50 is inserted through the skin of a patient at a desired location and plunger 25 is pushed to inject a controlled amount of neurotoxin into the patient. As neurotoxin is injected into the patient using syringe assembly 5, dosage markings 30 (in combination with marking 60 at junction 45) are used to visually indicate to the user the amount of neurotoxin which has been injected into the patient at each localized site of injection. The distinct contrast of marking 60 at junction 45 against the clear syringe barrel 20 ensures that the user can readily take note of dosage amounts by checking where marking 60 aligns with dosage markings 30 during and/or after an injection (e.g., marking 60 aligns with the 0.9 cc dosage marking before pushing plunger 25, and then marking 60 aligns with the 0.8 cc dosage marking after pushing plunger 25 to show that 0.1 cc (i.e., 5 units) of neurotoxin has been injected into the patient).

During the procedure, needle 50 may be replaced as necessary as the user of syringe assembly 5 moves between various injection sites. This ensures that the needle remains sharp for each injection. It should be appreciated that replacing needle 50 between injections increases comfort for the patient throughout a procedure. Once the procedure is completed, syringe assembly 5 is discarded. It should also be appreciated that syringe assembly 5 contains very little to no waste of neurotoxin when discarded due to inverted plunger tip 40 of plunger 25 not allowing any neurotoxin to be trapped in sealing hub 55 of needle assembly 35. In this way, the use of syringe assembly 5 also decreases the expense of many localized injection procedures.

It should be appreciated that modifications can be made to the syringe assembly of the present invention while still remaining within the scope of the present invention. By way of example but not limitation, and looking now at FIG. 6, an alternative plunger 25A is shown.

Figure 6:
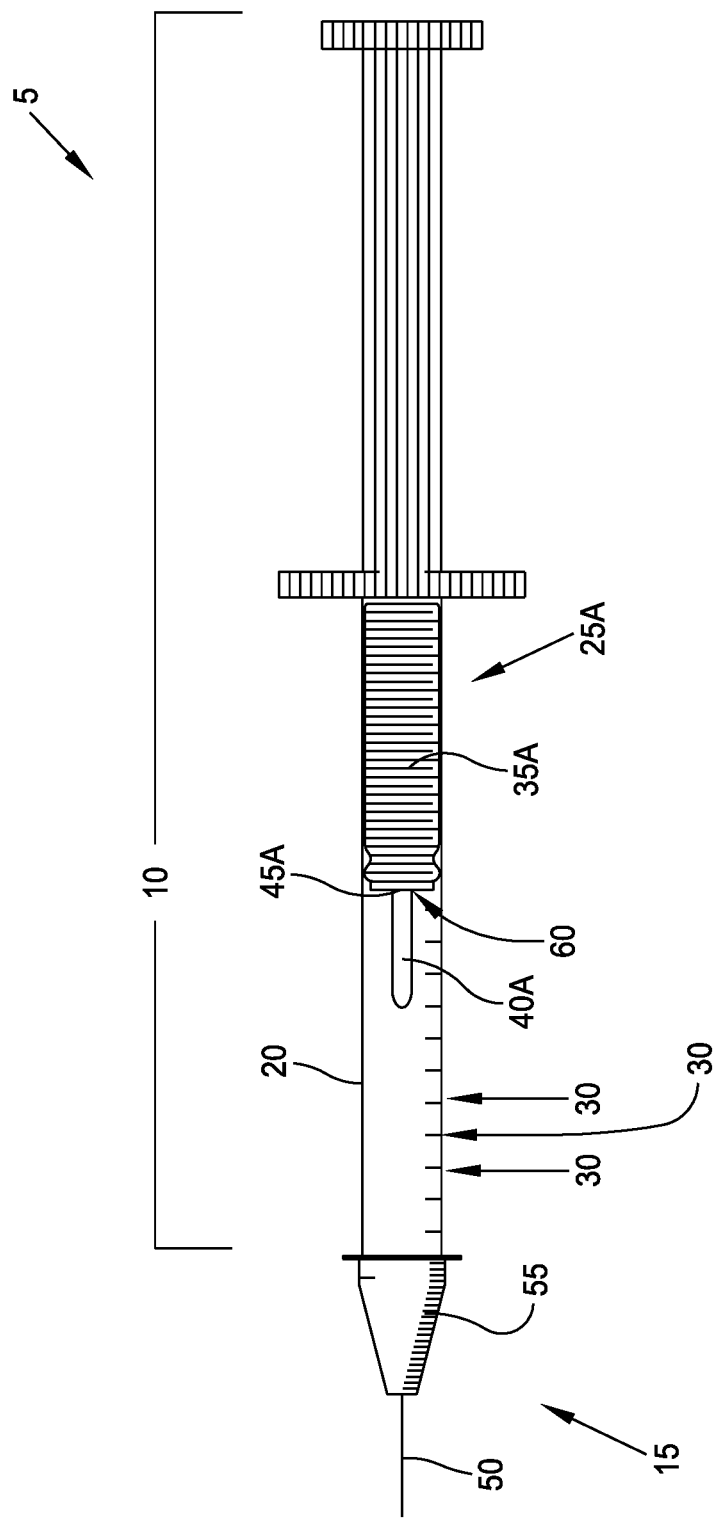
FIG. 6 is a schematic view of the syringe assembly of the present invention with an alternative plunger.

In FIG. 6, plunger 25A is similar to the plunger 25 discussed above, however, plunger body 35A is colored (instead of clear or opaque). Unlike conventional plunger tips (which typically are the same color as the plunger body), the clear inverted plunger tip 40A of FIG. 6 is a different color than plunger body 35A, whereby the point of color change provides a junction 45A which can be easily seen by a clinician as the plunger moves past the dosage markings on the syringe barrel.

When junction 45A is aligned with a dosage marking 30 on syringe barrel 20, a clinician can determine the amount of neurotoxin contained within syringe barrel 20 and/or determine the amount of neurotoxin that has been delivered to the patient. Since junction 45A is visually distinct on plunger 25, a clinician can visually control the amount of neurotoxin in syringe barrel 20, which significantly improves dosage accuracy.

Whether plunger body 35 is clear, opaque or colored, it is important to note that plunger body 35 is clear, opaque or colored so that the plunger body is distinct in the clear syringe barrel, and the plunger tip is clear so that the clinician can visually distinguish between the end of the plunger body and the plunger tip so that it will be easier for a clinician to align the end of the plunger body with the appropriate dosage marking on syringe barrel 20. The clear plunger tip of the present invention is also less distracting than plungers which are one color with no marking between the plunger body and the plunger tip.

In summary, the present invention provides a new and improved syringe assembly for neurotoxin injections having a syringe and a removable needle assembly, wherein the syringe comprises (i) a clear syringe barrel capable of holding 1.0 cc and including dosage markings which completely encircle the syringe barrel, and (ii) a plunger, wherein the plunger comprises a clear (or opaque) plunger body and a clear inverted plunger tip, with a marking at the distal end of the plunger body to mark the end of the plunger body, thereby clearly showing where to align the plunger body with the dosage marking on the syringe barrel, and further wherein the needle used for the neurotoxin injection is short and narrow (e.g., a 0.25 inch, 33 gauge needle).

Significantly, all of these features are combined into a single syringe assembly so as to provide a number of improvements over a conventional syringe assembly.

More particularly, the use of a short needle (i.e., 0.25 inch) having a narrow gauge (i.e., 33 gauge) allows for the precise placement of the needle in the body of a patient, thereby minimizing the potential for over-penetration and/or diffusion of the neurotoxin away from the intended site of injections. This in turn increases patient comfort and causes less bruising during injection and decreases the risk of unwanted side effects in a patient.

It should be appreciated that the removable needle assembly of the present invention allows a clinician to draw neurotoxin into the syringe with one size of needle attached to the syringe, and then remove and replace the needle with another size needle. In this way, a clinician may draw neurotoxin into the syringe barrel with a larger needle so as to fill the syringe faster, and then remove the larger needle and replace the larger needle with a smaller needle (i.e., the 33 gauge, 0.25 inch needle of the present invention) more appropriate for the procedure to be conducted on a patient.

Furthermore, by attaching the needle to the syringe with a removable needle tip, a dull needle can be removed from the syringe and replaced with a sharp needle without having to discard the entire syringe assembly (i.e., the syringe and the needle), which reduces waste and time. A needle attached to the syringe by a removable needle tip allows the needle to be changed multiple times as different sites are injected, which in turn leads to less pain for the patient. Additionally, where a procedure requires multiple injections using the same syringe, the smaller size needle may be replaced as needed (e.g., if the needle dulls) in order to increase patient comfort and provide more accurate dosing from the fine sharp tip of the narrow gauge needle.

It should also be appreciated that the provision of a syringe barrel with non-obstructed calibrations (i.e., dosage markings that completely encircle the syringe barrel) is a significant improvement over conventional syringe assemblies because the dosage markings are now visible to the clinician along the entire circumference of the syringe barrel. This significantly improves the dosing accuracy since a clinician no longer has to turn the syringe in order to read the dosage markings on one side of the syringe in order to determine the amount of neurotoxin contained within the syringe barrel. This, in turn, also leads to less discomfort for the patient.

It should be further appreciated that the clear inverted plunger tip allows for complete expulsion of neurotoxin from syringe 10, which reduces waste and decreases costs and is also less distracting for the clinician.

It is important to note that any appropriately sized syringe may be used in connection with the present invention, as long as the syringe is compatible with different size (i.e., gauge and length) needles. However, by providing a syringe with a larger capacity than conventional syringes, the syringe can accommodate many units of neurotoxin which will enable one syringe to be used for injecting the neurotoxin into multiples sites. This will also reduce waste and costs associated with neurotoxic delivery.

Each of the improvements provided by the syringe assembly of the present invention are significant because there is currently no antidote for the adverse side effects associated with inaccurate dosing or diffusion of the neurotoxin from the intended injection site. The better accuracy provided by the syringe assembly of the present invention will reduce side effects while also working to establish a universal syringe assembly that can be used by all clinicians delivering neurotoxins to patients.

Modifications

While the present invention has been described in terms of certain exemplary preferred embodiments, it will be readily understood and appreciated by those skilled in the art that it is not so limited, and that many additions, deletions and modifications may be made to the preferred embodiments discussed above while remaining within the scope of the present invention.

What is claimed is:

1. A syringe assembly for administration of a neurotoxin, the syringe assembly comprising: a syringe comprising: a clear syringe barrel with dosage markings completely encircling the clear syringe barrel, wherein each of the dosage markings is visible to a clinician when the clear syringe barrel is oriented at any rotational angle relative to a longitudinal axis thereof; and a plunger having a plunger body, a clear inverted plunger tip, and a marking disposed at a junction between the plunger body and clear inverted plunger tip, the marking comprises a color that is visible to the clinician through the clear syringe barrel from an exterior of the syringe assembly and has a contrasting appearance relative to each of the dosage markings; and a needle assembly comprising a needle and a sealing hub for removably attaching the needle assembly to the syringe, wherein the needle is approximately 0.15 inches to approximately 0.3 inches in length and has a gauge of approximately 27 gauge to approximately 35 gauge.

2. The syringe assembly according to claim 1, wherein the syringe is a 1.0 cc syringe.

3. The syringe assembly according to claim 1, wherein the dosage markings are cc markings.

4. The syringe assembly according to claim 1, wherein the dosage markings are unit markings.

5. The syringe assembly according to claim 1, wherein the unit markings are derived based on dilution of a medicament to be delivered by said syringe assembly.

6. The syringe assembly according to claim 1, wherein the dosage markings are both unit markings and cc markings.

7. The syringe assembly according to claim 1, wherein the plunger body is clear.

8. The syringe assembly according to claim 1, wherein the plunger body is opaque.

9. The syringe assembly according to claim 1, wherein the plunger body and inverted tip are different colors.

10. The syringe assembly according to claim 1, wherein the needle is 0.25 inches in length.

11. The syringe assembly according to claim 1, wherein the needle is 33 gauge.

12. The syringe assembly according to claim 1, wherein the marking enhances visual distinction between the plunger body and the inverted plunger tip.

13. The syringe assembly according to claim 1, wherein the neurotoxin is botulinum toxin.

14. The syringe assembly according to claim 1, wherein thickness of said dosage markings is graduated from lowest dosage to highest dosage.

15. The syringe assembly according to claim 1, wherein darkness of said dosage markings is graduated from lowest dosage to highest dosage.

\* \* \* \* \*